United States Patent [19]

Nakayasu et al.

[11] Patent Number: 5,037,804
[45] Date of Patent: Aug. 6, 1991

[54] AGENT FOR PREVENTING AND TREATING THROMBOCYTOPENIA

[75] Inventors: Toshiro Nakayasu; Ken Masuo; Teruo Takayanagi; Atsuo Inoue, all of Tokyo; Eiro Tsubura, Hyogo; Toru Masaoka, Osaka, all of Japan

[73] Assignee: Daiichi Seiyaku Co., Ltd., Tokyo, Japan

[21] Appl. No.: 381,718

[22] PCT Filed: Sep. 2, 1988

[86] PCT No.: PCT/JP88/00883
§ 371 Date: Jun. 8, 1989
§ 102(e) Date: Jun. 8, 1989

[87] PCT Pub. No.: WO89/01778
PCT Pub. Date: Mar. 9, 1989

[30] Foreign Application Priority Data

Sep. 2, 1987 [JP] Japan .................... 62-219937

[51] Int. Cl.[5] .................... A61K 37/02; C07K 9/00
[52] U.S. Cl. .................... 514/8; 530/322
[58] Field of Search .................... 514/8; 530/322

[56] References Cited

U.S. PATENT DOCUMENTS

| | | | |
|---|---|---|---|
| 4,357,322 | 11/1982 | Rooks, II et al. | 514/8 |
| 4,382,080 | 5/1983 | Shiba et al. | 514/8 |
| 4,684,625 | 8/1987 | Eppstein et al. | 514/8 |
| 4,780,313 | 10/1988 | Koichiro et al. | 514/8 |
| 4,895,835 | 1/1990 | Hasegawa | 530/322 |

FOREIGN PATENT DOCUMENTS 62-27079  6/1987  Japan .................... 514/8

*Primary Examiner*—Lester L. Lee
*Attorney, Agent, or Firm*—Sughrue, Mion, Zinn Macpeak & Seas

[57] ABSTRACT

The present invention relates to an agent for preventing and treating thrombocytopenia which comprises, an an active ingredient, a muramyldipeptide derivative of the formula:

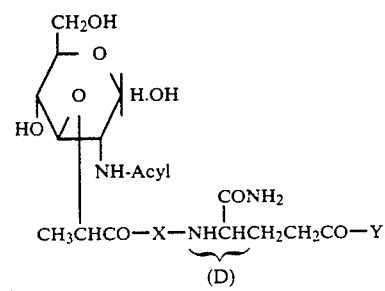

(D)

wherein X represents an amino acid residue selected from L-alanine, L-serine and L-valine, Y represents

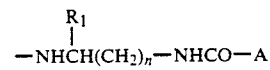

wherein $R_1$ represents a carboxyl group, n represents an integer of 1 to 6, A represents a saturated aliphatic hydrocarbon group having 7 to 29 carbon atoms which may have branched chains, and Acyl represents an acyl group having 2 to 6 carbon atoms, and the agent exhibits excellent preventing and treating effects on thrombocytopenia when administered orally or parenterally.

4 Claims, No Drawings

AGENT FOR PREVENTING AND TREATING THROMBOCYTOPENIA

TECHNICAL FIELD

This invention relates to an agent for preventing and treating thrombocytopenia which comprises, as an active ingredient, a muramyldipeptide derivative represented by the formula (I):

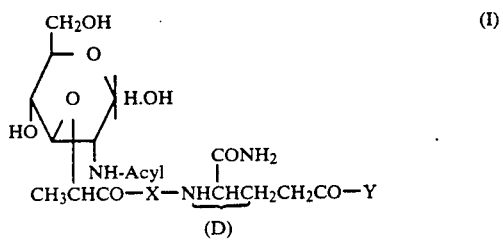

(D)

wherein X represents an amino acid residue selected from L-alanine, L-serine and L-valine, Y represents

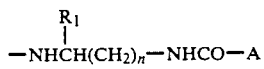

wherein $R_1$ represents a carboxyl group, n represents an integer of 1 to 6, A represents a saturated aliphatic hydrocarbon group having 7 to 29 carbon atoms which may have branched chains, and Acyl represents an acyl group having 2 to 6 carbon atoms.

TECHNICAL BACKGROUND

Multipotential stem cells, which can differentiate to granulocytes, monocytes (macrophages), red blood cells, platelets, lymphocytes, exist in the bone marrow of higher animals such as human and mouse. The stem cells differentiate to precursory cells and the cells differentiate to the above blood cells. On the differentiation to these blood cells, several specific growth factors have been known to function to each blood cell's differentiation. For example, Interleukin-3 functions to the multipotential stem cells to induce the differentiation thereof to precursory granulocytes, and the granulocyte growth factors such as granulocyte-colony stimulating factor (G-CSF, etc.) function to the precursory cells to induce the differentiation thereof and to mature into granulocytes. With respect to the platelets, precursory cells such as megakaryocytes and platelet growth factor (MK-CSF) participate in the platelets. However, the details thereof have not been clarified.

Of various platelets which are considered to have maturation function, platelets have a significant role to maintain the health independently or in cooperation with other blood cells. Therefore, when the differentiation to platelets is inhibited, some diseases caused by reduction of platelet numbers appear.

Examples of such diseases include symptomatic thrombocytopenia, idiophatic thrombocytopenia and the like caused by medical agents (an anticancer agent, etc.), radiation, blood diseases, etc., and more specific symptoms thereof include bleeding, coagulation defect and the like.

Conventionally, as the treating method for such various thrombocytopenia, only platelets transfusion which is complicated and expensive has been used. Thus, there was no agent for the prevention and treatment of such symptoms.

The compounds of the present invention are disclosed in Japanese Patent Publication No. 62-27079 filed by the applicant as having an excellent adjuvant activity and/or preventing and treating effects on infection by microorganisms. However, it has been unknown that the compounds of the formula (I) are effective for the prevention and treatment of thrombocytopenia.

DISCLOSURE OF THE INVENTION

As a result of extensive studies on the compounds of formula (I) above, the present inventors found that the compounds exhibit excellent effects on prevention and treatment of thrombocytopenia and completed the present invention.

That is, the present invention relates to an agent for preventing and treating thrombocytopenia which comprises a compound of the formula (I) as an active ingredient.

Pharmaceutical preparations for administering the compound of the formula (I) include tablets, capsules, powders, granules, injections, suppositories, sprays, dermal preparations and the like. These preparations can be prepared by known pharmaceutical techniques using appropriate additives such as excipients, e.g., corn starch, lactose, mannitol, etc., binders, e.g., hydroxypropyl cellulose, polyvinyl pyrrolidone, etc., disintegrators, e.g., low substituted hydroxypropyl cellulose, crystalline cellulose, etc., and lubricants, e.g., talc, magnesium stearate, etc. If desired, the preparations of the present invention can be a slow release preparation which can be prepared using known pharmaceutical techniques.

The pharmaceutical agent of the present invention thus prepared can be administered orally or parenterally. The dose level usually ranges from 100 to 400 μg/day for adult in case of subcutaneous administration. The therapeutic effect of the agent according to the present invention is expected to be further enhanced by combining with whole blood transfusion or platelets transfusion which is a typical conventional therapeutic method for thrombocytopenia.

The compounds of the present invention are of low toxicity. For example, $LD_{50}$ of Compound A described below which is a typical compound was found to be 600 to 1,000 mg/kg in rats by subcutaneous injection.

THE BEST MODE FOR CONDUCTING THE INVENTION

The present invention is hereinafter described with reference to Reference Example and Examples, but the present invention is not limited to these examples.

EXAMPLE 1

Preparation of vial of main agent

| A vial containing: | |
|---|---|
| Compound A | 0.2 mg |
| D-Mannitol | 45.0 mg |
| Potassium dihydrogen phophate | 1.95 mg |
| Sodium hydrogen phosphate | 8.31 mg |
| An additive solution for dissolution | 1 ml |
| An ampule containing: | |
| Distilled water for injection | |

According to the above furmulation, a lyophilized injection containing 200 μg was preapred using known pharmaceutical techniques. This preparation is used by dissolving in the additive solution just before use.

EXAMPLE 2

Compound A (200 μg) was administered subcutaneously to 20 patients with malignant lymphoma in a single daily dose for 10 consecutive days from 3 to 5 days after the starting day of chemotherapy for the above disease. Blood test was carried out on the 7, 10, 14, 17, 21 and 24th days from the starting day of the chemotherapy. The number of platelets was compared with that in the same patients of non-medication by the cross over method. The results are shown in Table 1 below as mean ± standard error.

*Compound A: An anomeric mixture of $N^2$-[(N-acetylmuramyl)-L-alanyl-D-isoglutaminyl]-$N^6$-stearoyl-L-lysine

TABLE 1

| Platelet Numbers[a] at the Starting Day of Chemotherapy | Platelet Numbers[a] (difference from the previous value) | | | | | |
|---|---|---|---|---|---|---|
| | 7th Day | 10th Day | 14th Day | 17th Day | 21th Day | 24th Day |
| Administered Group 25.7 ± 1.9 | −4.3 ± 1.7 | −7.2 ± 1.6 | −4.4 ± 2.3 | 3.8 ± 1.8* | 5.9 ± 2.0** | 0.7 ± 2.1 |
| Control Group 28.6 ± 2.5 | −8.9 ± 2.4 | −10.7 ± 2.7 | −8.0 ± 2.8 | −2.3 ± 2.6 | −3.5 ± 2.4 | −3.5 ± 3.3 |

[a]Platelet numbers × $10^4$/mm$^3$
*The difference was significant at the level of 5% or less, as a result of analysis by the paired t-test.
**The difference was significant at the level of 1% or less, as a result of analysis by the paired t-test.

As is apparent from the results in Table above, the increase in the platelet numbers was observed by administration of Compund A, and a tendency to suppress the reduction in the platelet numbers caused by the anticancer agent and to restore the platelet numbers was observed.

APPLICABILITY IN INDUSTRIAL FIELD

The compound of formula (I) exhibits excellent prevention and treatment effects of thrombocytopenia and, therefore, is excellent as an agent for preventing and treating the thrombocytopenia.

What is claimed is:

1. A method for preventing or treating thrombocytopenia comprising administering to a subject an antithrombocytopenia effective amount of a muramyldipeptide derivative of the formula:

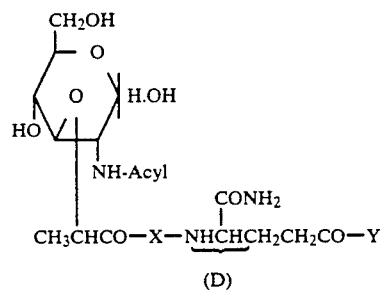

(D)

wherein X represents an amino acid residue selected from L-alanine, L-serine and L-valine, Y represents $$-NHCH(CH_2)_n-NHCO-A$$
$$\phantom{-NHCH(CH_2)_n-NH}|$$
$$\phantom{-NHCH(CH_2)_n-NHCO-}R_1$$

wherein $R_1$ represents a carboxyl group, n represents an integer of 1 to 6, A represents a saturated aliphatic hydrocarbon group having 7 to 29 carbon atoms which may have branched chains, and Acyl represents an acyl group having 2 to 6 carbon atoms.

2. The method of claim 2, wherein the antithrombocytopenia effective amount of muramyldipeptide derivative present ranges from about 100 to 400 μg/day.

3. The method of claim 2, wherein the composition is administered to a subject by subcutaneous injection.

4. The method of claim 2, wherein the muramyldipeptide derivative is an anomeric mixture of $N^2$-[(N-acetylmuramyl)-L-alanyl-D-isoglutaminyl]-$N^6$-stearoly-L-lysine.

* * * * *